United States Patent [19]

Patel et al.

[11] Patent Number: 5,346,642
[45] Date of Patent: * Sep. 13, 1994

[54] HAIR CONDITIONING SHAMPOO CONTAINING LONG CHAIN ALCOHOL COMPONENT

[75] Inventors: Amrit M. Patel, Dayton; Clarence R. Robbins, Martinsville, both of N.J.

[73] Assignee: Colgate-Palmolive Company, New York, N.Y.

[*] Notice: The portion of the term of this patent subsequent to Mar. 5, 2008 has been disclaimed.

[21] Appl. No.: 984,786

[22] Filed: Dec. 3, 1992

Related U.S. Application Data

[63] Continuation of Ser. No. 507,335, Apr. 9, 1990, Pat. No. 5,213,716, which is a continuation-in-part of Ser. No. 432,644, Nov. 7, 1989, Pat. No. 5,051,250, which is a continuation-in-part of Ser. No. 432,952, Nov. 7, 1989, abandoned, which is a continuation-in-part of Ser. No. 369,361, Jun. 21, 1989, abandoned.

[51] Int. Cl.$^5$ .................. C11D 1/68; C11D 3/20; C11D 3/37
[52] U.S. Cl. .................. 252/174.21; 252/547; 252/550; 252/551; 252/174.15; 252/174.23; 252/DIG. 13; 424/70
[58] Field of Search ........... 252/547, 550, 551, 174.15, 252/174.23, 174.21, DIG. 13; 424/70

[56] References Cited

U.S. PATENT DOCUMENTS

| 4,765,975 | 8/1988 | Iovanni et al. | 424/70 |
|---|---|---|---|
| 4,842,850 | 6/1989 | Vu | 424/70 |
| 4,855,130 | 8/1989 | Konrad et al. | 424/70 |
| 4,950,468 | 8/1990 | Nakamura | 424/70 |
| 4,997,641 | 3/1991 | Hartnett et al. | 424/70 |
| 4,999,120 | 3/1991 | Seemuth | 252/8.6 |
| 5,051,250 | 9/1991 | Patel et al. | 424/70 |
| 5,106,613 | 4/1992 | Hartnett et al. | 424/71 |
| 5,213,716 | 5/1993 | Patel et al. | 252/547 |

FOREIGN PATENT DOCUMENTS 59-184115 10/1984 Japan .

OTHER PUBLICATIONS

English translation of JP-59184115 Oct. 1984.

*Primary Examiner*—Paul Lieberman
*Assistant Examiner*—Erin M. Higgins
*Attorney, Agent, or Firm*—Robert C. Sullivan; Richard J. Ancel

[57] ABSTRACT

A fiber conditioning composition, which is preferably a shampoo for human hair, in stable and pearlescent liquid or semi-liquid or gel condition, is an emulsion or dispersion which includes a surfactant, a water insoluble fiber conditioning agent, a long chain saturated primary alcohol or derivative thereof, which stabilizes the emulsion or suspension and makes it pearlescent, and an aqueous medium, which may also contain other components of such fiber conditioning and shampoo compositions. In the preferred shampoos an anionic detergent is present, which is preferably a mixture of higher fatty alcohol sulfate and higher fatty alcohol ethoxylate sulfate, the long chain saturated primary alcohol (or derivative) is of an average of 30 to 40 carbon atoms (ethoxylated such alcohols may also be employed, at least in part) and the water insoluble conditioning agent is a silicone (very preferably a certain type of aminosilicone), a polyethylene, a paraffin, an isoparaffin, a microcrystalline wax, a $C_{18-36}$ *(mixed)* fatty acid or triglyceride, a higher fatty alcohol ester of a higher fatty acid (such as stearyl stearate), beeswax, or any mixture thereof, with the more preferred shampoos containing conditioning agents which include the aminosilicone in mixture with one or more of the polyethylene, microcrystalline wax, petrolatum, paraffin and isoparaffin, plus a cationic hair conditioning agent, which is preferably a quaternary ammonium salt. The disclosed invention also includes processes in which the compositions are used to condition or to clean and condition fibrous materials, such as human hair on the head.

17 Claims, No Drawings

HAIR CONDITIONING SHAMPOO CONTAINING LONG CHAIN ALCOHOL COMPONENT

This is a continuation of application Ser. No. 07/507,335 filed, Apr. 9, 1990 now U.S. Pat. No. 5,213,716 which is a continuation in part of Ser. No. 07/432,644 filed Nov. 7, 1989, now U.S. Pat. No. 5,051,250, which is a continuation in part of Ser. No. 07/432,952 filed Nov. 7, 1989 now abandoned which is a continuation in part of Ser. No. 07/369,361 filed Jun. 21, 1989 now abandoned.

This invention relates to fiber conditioning compositions. More particularly, it relates to hair conditioning compositions, especially shampoos, which are useful to clean human hair while simultaneously conditioning it, so that it will be more easily manageable (combable and of relatively low static charge) after shampooing than if it had been washed with a conventional shampoo.

Hair conditioning shampoos are well known in the cosmetic art and are described in various patents and patent applications. Cationic surfactants, such as quaternary ammonium salts, have been employed in hair rinses and in shampoos as conditioning agents, as have been various silicones and other water insoluble conditioning agents, including waxes, greases and oils. Shampoos have been made in solid, gel, creme, and liquid forms, and in liquid form they have been produced as solutions, emulsions, and suspensions or dispersions. When shampoos are in emulsion or suspension (or dispersion) form sometimes they tend to separate on storage, which separation should be prevented in products intended for commercial applications. The present invention provides a fiber conditioning composition, preferably a conditioning shampoo, which includes a water insoluble conditioning agent and a long chain saturated primary alcohol or derivative, of a chain length in a certain range, which, it has been found, stabilizes the emulsion or suspension, makes it desirably pearlescent, and also improves the hair conditioning effect thereof.

In accordance with the present invention a pearlescent fiber conditioning composition, preferably a shampoo, in stable emulsion or suspension form, comprises a surface active agent (surfactant), a waiter insoluble fiber conditioning agent, a long chain saturated primary alcohol of an average of 25 to 45 carbon atoms, or a derivative thereof, in sufficient proportion to stabilize the emulsion or suspension and to make it pearlescent, and an aqueous medium, which may include adjuvants and other components of such fiber conditioning compositions. The presence of the long chain alcohol or derivative thereof also often improves conditioning of the treated fiber.

A search of the prior art resulted in the finding of the following U.S. Pat. Nos.:

| | | |
|---|---|---|
| 3,969,500; | 4,707,293; | 4,824,602; |
| 4,470,982; | 4,726,944; | 4,850,732; |
| 4,701,322; | 4,728,457; | 4,885,130 and |
| 4,704,272; | 4,803,237; | 4,859,500. |

Also of interest is the Petrolite Corporation brochure entitled Unilin ™ Alcohols, copyrighted in 1985 and identified as SP-1040.

In another application which is being filed on the same day as the present application and is entitled Improved Hair Conditioning Shampoo (Hartnett et al.), there are described shampoos like those of the present invention in which the anionic detergent component is of a certain type, which includes a shorter chain alkyl group, preferably an octyl or decyl group, as the lipophile thereof. Such application represents an improvement of the present invention and necessarily discloses much of what is described herein.

Although the art found describes pearlescent shampoos and the incorporation of various conditioning agents into shampoos, and establishes that the long chain alcohols that are components of the invented compositions are known materials, applicants are unaware of any teaching in any of the references or in any combination thereof that would lead one to the present invention or that would lead one to expect to obtain the advantages thereof.

In a broader aspect of this invention the fiber conditioning composition thereof may be in liquid, creme, gel or paste form and needs only to comprise water insoluble fiber conditioning agent and long chain saturated primary alcohol in an aqueous medium, preferably with cationic fiber conditioning agent (which is also a surfactant but here will be considered as in the class of conditioning agents) also being present. In some such forms stabilization, which is effectable by the long chain saturated primary alcohol (for ease of expression "or derivative" will often be omitted henceforth), may be unnecessary, but other advantages of such compounds are also obtainable, including pearlescing effect and improvement in conditioning. In the hair conditioning shampoo there will also be present a water soluble synthetic organic detergent, preferably an anionic detergent, more preferably a higher alkyl sulfate and/or higher alkyl ethoxy sulfate. Such compositions may be in various non-liquid forms but preferably are in emulsified or suspended (or dispersed) form in an aqueous medium, and preferably are liquids.

Of the water insoluble fiber conditioning agents those which are more preferred include: organosilicon compounds, e.g., non-volatile silicones (especially aminesilicones), which include dimethicones; polyethylenes; paraffins; petrolatums; microcrystalline waxes; $C_{18-36}$ (mixed) fatty acids and corresponding triglycerides; steary stearate; and quaternary ammonium and amine salts (which are classified herein with conditioning agents rather than with surfactants, although they act as both). The organosilicon compounds and silicones that may be employed include any of those which are conditioning agents for fibrous materials, various of which have been described in the previously mentioned patents and applications. However, it has been found that aminesilicones are usually more effective conditioning agents in the compositions of this invention than are conventional silicones, and of the aminesilicones the present types are better yet. Thus, it is much preferred to utilize an aminesilicone of the formula

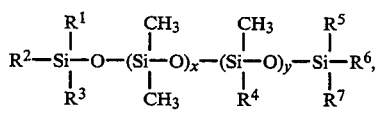

wherein $R^1$, $R^2$, $R^3$, $R^5$, $R^6$ and $R^7$ are alkyls of 1 to 6 carbon atoms, and most preferably of 1 carbon atom each, $R^4$ is $-R^8-NH-CH_2CH_2-NH_2$, $R^8$ is alkylene of 3 to 6 carbon atoms, and most preferably is an isobutyl group, x is an average number in the range of 100 to 10,000, and y is an average number in the range of 1 to 10, more preferably less than 5, and most preferably 1, which is of an amine equivalent in the range of 4,000 to 60,000. Preferably, x is in the range of 200 or 300 to 10,000, more preferably 500 to 10,000, and most preferably 750 to 800 or 850, e.g., about 800, and y is in the range of 0 to 8, more preferably being less than 3 and most preferably being about 1. The amine equivalent of such aminosilicone is preferably in the range of 5,000 to 50,000, more preferably 10,000 to 40,000. For the specific preferred aminosilicone utilized in the experiments reported in this specification the molar percentage of amine is about 0.125, the degree of polymerization is about 800, x is 797, y is one, and the molecular weight may be about 60,000 daltons. Because molecular weights of high polymers sometimes vary, depending on the measurement technique utilized, it is suggested that primary reference should be to the formula for identification of the aminosilicones described, rather than placing primary reliance on the molecular weights given. The described preferred aminosilicone is available from bow Corning Corporation, and it is identified in the working examples herein as bow Corning Aminosilicone A (applicants' identification).

The polyalkylenes that may be employed as water insoluble conditioning agents in the present compositions are preferably those of a molecular weight in the range of 1,000 to 5,000, more preferably 1,000 to 4,000 and still more preferably 2,000 to 2,500, e.g., about 2,000. Oxidized versions of these polyalkylene polymers may also be used, which create larger hydrocarbons with terminal carboxyl groups. Although the alkylenes of these polymers will usually be ethylene, it is within the invention to employ polymers of hydrocarbons of 1 to 5 carbon atoms each, preferably 2 to 3 carbon atoms, in which the molecular weight range may be from 1,000 to 10,000, or even more, under some conditions. Usually however, the polymers will be of ethylene and/or propylene, and almost always of ethylene (polyethylene).

Paraffins that may be utilized will normally be of chain lengths of 20 to 50 carbon atoms, preferably 20 to 40 carbon atoms, and isoparaffins can be of chain lengths in the range of 12 to 16 carbon atoms, preferably 13 to 14 carbon atoms. The petrolatums are petroleum jellies or mineral jellies which melt in the range of 38° to 60° C. and the microcrystalline waxes are of an average molecular weight in the range of about 500 to 800 (which is about twice that of the paraffins). $C_{18-36}$ fatty acids and corresponding triglycerides are higher fatty acids and triglycerides which are available from Croda Chemical Corporation(under the tradename Syncrowax HGL-C, for example, for the triglycerides). Stearyl stearate, which is representative of useful esters of both higher fatty alcohols and higher fatty acids, is available from Inolex Corporation, as Lexol SS.

The cationic conditioning agents (which may be considered to be secondary conditioning agents in the invented conditioning compositions) are preferably quaternary ammonium salts, although other cationic compounds of fiber conditioning properties may also be employed, at least in part. Thus, known amines, amine salts, imidazolinium salts and betaines, and such cationic materials as are described in U.S. Pat. No. 4,000,077 may be substituted for at least some of the quaternary ammonium salt, as may be complexes of cationic and anionic surfactants, such as have been described in U.S. Pat. Nos. 4,896,422 and 4,888,119 and in U.S. patent application Ser. No. 06/916,069.

The preferred quaternary ammonium salts are of the formula $R^9$, $R^{10}$, $R^{11}$, $R^{12} N^+ X^-$, wherein at least one of the R groups is lower alkyl and at least one is higher alkyl, with the others being higher and/or lower alkyl. Preferably $R^9$ is lower alkyl, such as of 1 to 4 carbon atoms, $R^{10}$ and $R^{11}$ are higher alkyls of 10 to 40 carbon atoms, $R^{12}$ is such a higher alkyl or lower alkyl, and $X^-$ is a salt-forming anion, such as halide, lower alkosulfate or lower carboxylic acid radical, e.g., chloride, bromide, methosulfate, ethosulfate, citrate or acetate. The lower alkyl will preferably be of 1 to 3 carbon atoms, more preferably being of 1 or 2 carbon atoms, and most preferably, in most cases, will be methyl, and the higher alkyl will preferably be of 10 to 22 carbon atoms, more preferably 12 to 18 or 20 carbon atoms, most preferably of 14 to 18 carbon atoms, e.g., 16 or 18 carbon atoms. The anion is preferably a halogen, such as chlorine, bromine or iodine, with chloride and bromine being preferred and with chlorine being more preferred.

The number of lower alkyls on the quaternary nitrogen will preferably be 1 or 2 and the number of higher alkyls will usually be 2 or 3. Thus, such compounds have 2 or 3 long chain alkyls and 2 or 1 short chain alkyl(s) of 12 to 20 and 1 or 2 carbon atoms, respectively. It has been found to be desirable to have at least 30 carbon atoms in the quaternary ammonium salt and preferably at least 34. The most preferred higher alkyls are cetyl and stearyl and the most preferred lower alkyl is methyl. The more preferred quaternary ammonium halides include tricetyl methyl ammonium chloride and distearyl dimethyl ammonium chloride, but other such quaternary ammonium salts, are also operative, including dicetyl dimethyl ammonium chloride and tristearyl methyl ammonium chloride, corresponding bromides, amines, amine salts, betaines and complexes of the previously mentioned U.S. patents, which are hereby incorporated by reference. Such alternative cationic surfactants and complexes may be employed as at least part of the cationic surfactant content of the invented compositions.

The long chain primary alcohol of the compositions of this invention is preferably a saturated compound, with the hydroxy group being terminally located. Such alcohol will normally be of a distribution of homologous alcohols and typically all are of even numbers of carbon atoms, averaging 24 to 45 carbon atoms (on a weight basis), preferably 28 to 42 carbon atoms, more preferably about 30 to 40 carbon atoms and most preferably 30 to 40 carbon atoms. When the average number of carbon atoms in the chain is less than 24 the desired effectiveness of such alcohols in the present formulations is decreased, with the stabilization, fiber conditioning and pearlescing actions being diminished, and when such chain length is more than 45 carbon atoms, e.g., of an average of about 50 carbon atoms, such alcohols are not satisfactorily dispersible in the described compositions. In addition to the mentioned long chain alcohols, related compounds such as corresponding alkoxylated alcohols, corresponding fatty acids and long chain saturated primary alcohol esters, may be substituted, at least in part. Of such "derivatives" the alkoxylated alcohols are preferred, and the most preferred of these are the ethoxylated alcohols, which will normally contain up to about 20 ethoxy groups per mole, e.g., about 10 to 20. However, the alcohols, which are the preferred embodiments of the invention, normally will be employed alone or in mixture with related compounds from the "derivatives" group, with the alcohol being the major proportion of the total "alcohol plus derivatives" content. Examples of commercial materials which may be employed in the present compositions are those manufactured by Petrolite Corporation and sold through their Petrolite Specialty Polymers Group under the name Unilin TM Alcohols, as described in the technical bulletin previously referred to in this specification. Such alcohols may be 75 to 90%, e.g., 80 to 85%, of the commercial product, with the balance of such products being substantially all saturated hydrocarbons of corresponding chain lengths. In such products the distribution curve for the alcohol is substantially bell-shaped, with no chain length of alcohol being more than 10% of the total content thereof, and with the corresponding hydrocarbon content being of a substantially flat distribution curve, with about 1 or 2% of each of the hydrocarbons being present. Such distribution curves, as bar graphs, are given in the Petrolite bulletin previously mentioned. The alcohols (and corresponding hydrocarbons) present will normally be of chain lengths such that at least 80% are in the range of 18 or 20 to 54 carbon atoms, with at least 80% being in the range of about 18 or 20 to 44 carbon atoms for an alcohol averaging about 30 carbon atoms and with at least 80% being in the range of about 28 or 30 to 54 carbon atoms when the alcohol averages about 40 carbon atoms. Examples of the long chain primary alcohols are Unilin-425 alcohol, which averages 30 carbon atoms in its chain, Unilin-550 alcohol, which averages 40 carbon atoms in its chain, and Unilin-350, which averages about 26 carbon atoms in its chain. A derivative, Unithox-550, is an ethoxylated such alcohol of an average of 40 carbon atoms in the alkyl chain, ethoxylated with up to 20 ethoxy groups, e.g., 13.

The water soluble synthetic organic anionic detergent, which is present in the shampoo embodiments of this invention, and may also be present in some conditioning embodiments, too, is normally a lipophile sulfate or sulfonate, although other hydrophile groups than sulfate and sulfonate may also be employed, such as phosphate and phosphonate. The salt forming cation of such compounds is normally alkali metal, ammonium or alkanolamine, with sodium and ammonium salts being preferred. It is also preferred for the anionic detergent to be a lipophile sulfate or a mixture of sulfates. The anionic detergent lipophile will be an alkyl group, preferably a higher fatty alkyl of 12 to 18 carbon atoms, although the increasingly broader ranges of 10, 8 and 6, or up to 18 or 20 carbon atoms, are also contemplated. Such detergents appear to be most compatible with the described shampoos and yield good cleaning and conditioning, while not interfering with pearlescing and conditioning effects of the composition. Particularly desirable detergents are ammonium lauryl sulfate and sodium lauryl ethoxyether sulfate having 1 to 6 ethoxy groups per mole, preferably 2 or 3.

Although the preferred anionic detergents are those described above, other such anionic detergents may be substituted, ate least in minor proportion, for them, and such other anionic detergents are described in *McCutcheon's Detergents and Emulsifiers*, North American Edition, published in 1984. Additionally, it may be desirable to employ amphoteric, ampholytic and zwitterionic detergents in such compositions and sometimes, relatively small proportions of nonionic detergents, and such are also described in such publication, which is hereby incorporated herein by reference. Also, see the description of suitable detergents in Ser. No. 07/432,952, previously referred to herein and incorporated by reference. Sometimes relatively small proportions of such surfactants, which term is used here in a broad sense and includes various emulsifiers and dispersing agents, too, may be employed in non-shampoo hair conditioners and fiber conditioning compositions.

For the preferred detergent combinations referred to above, those of higher fatty alkyl sulfate and higher fatty alkyl ethoxylate sulfate, the preferred proportions are in the ranges of 2:1-8:1 of alkyl sulfate to alkyl ethoxy sulfate and it is preferred that the alkyl sulfate be an ammonium salt and the alkyt alkoxy sulfate be a sodium salt. However, either such detergent may be employed alone and in in some preferred formulations the ethoxylated detergent has been omitted.

The various required components of the present compositions are dissolved and/or emulsified and/or suspended in an aqueous medium. Such medium may include various non-interfering normal fiber conditioning composition and shampoo composition constituents known in the art, but a few of these will be specifically mentioned herein because they are especially desirable components of the present composition and contribute in a significant manner to its desirable properties. Higher fatty alkanolamides have long been known as foaming agents and foam stabilizers. Such compounds will usually be of 12 to 16 carbon atoms in the acyl group, which is reacted with a lower (1 to 3 carbon atoms) mono- or dialkanolamine. In the present formulations the best alkanolamide is considered to be lauric monoethanolamide but cocodiethanolamide is of about equivalent effect. However, other known foam stabilizers and foaming agents may also be employed too, in whole or in part, such as the beta fries and related materials. Various gums and other thickening materials are also useful in shampoo compositions but it has been found that the best of these in the present compositions are hydroxyethyl celluloses. Such are available from Aqualon Corporation under the trademark Natrosol, such as Natrosol 250 HHR and Natrosol 330 CS, which preferably are employed in mixture, with the content of the former being from 2 to 5 times that of the latter. Although the hydroxyethyl celluloses are preferred, other such synthetic gums and thickeners, e.g., methyl cellulose, hydroxypropyl-methyl cellulose, Polyquaternum TM -10, modified starches, and natural gums and thickeners, e.g., guar gum, may be substituted, at least in part, depending on the product. Another important constituent of the present composition is mineral oil, when polyethylene is employed as a hair conditioning agent. The mineral oil is employed to solubilize and to help disperse the polyethylene, which, if not satisfactorily dispersed in the composition, will be of little hair conditioning effect and tends to settle out.

Other components which may be employed in the present compositions include: ethylene glycol monostearate, ethylene glycol distearate and propylene glycol distearate, all of which have pearlescing properties; viscosity control agents, such as propylene glycol and sodium chloride; pH adjusting agents, such as citric acid and citrates; sequestrants, such as EDTA; antifreezes, such as propylene glycol; solvents, such as ethanol and isopropanol; preservatives and antioxidants, such as Germaben II (Sutton Laboratories); anti-dandruff agents, such as zinc pyrithione or Climbazole TM (see U.S. Pat. No. 4,867,971); colorants and perfumes.

Water, employed to make the aqueous medium, which may be present not only in liquid preparations but also in gels, pastes and cremes, is preferably deionized and irradiated water of essentially zero hardness but it may also be tap water, although it is preferred to keep the hardness below 50 p.p.m., as calcium carbonate. However, other tap waters of hardnesses as high as 200 p.p.m. will sometimes also be useful, but usually they will be avoided.

The proportions of the various components present in the invented liquid conditioning and shampoo compositions to obtain the described desirable properties will now be given.

The surfactant content range, for both conditioning compositions, e.g., hair rinses, and shampoos, will be in the range of 1 to 35%, preferably 2 to 35%, and more preferably 3, 5 or 8 to 25% such ranges being lower for the "conditioning compositions" and higher for the shampoos. Such ranges for the shampoos are normally 5 to 35%, preferably 8 to 25 or 30% and more preferably 10 to 20%. For alkyl sulfate - alkyl ethoxylate sulfate shampoos ranges are usually 5 to 25%, preferably 10 to 20% and more preferably 10 to 15% of the former and up to 15%, preferably 0 or 1 to 10% and more preferably 0 or 1 to 5% of the latter. When either such sulfated detergent is employed alone the ranges for the alkyl sulfate apply.

The content of water insoluble conditioning agent(s) (excluding the content of cationic surfactant) will be a conditioning proportion or such a proportion which, in conjunction with the cationic surfactant present, serves satisfactorily to condition fibers or hair, which will normally be in the range of 0.3 to 10% for both fiber conditioning and shampoo compositions, preferably 0.3 to 7%, and more preferably 0.3 to 5%. The cationic surfactant is present in a fiber conditioning or conditioning supplementing proportion, which will normally be from 0.1 to 5%, for both fiber conditioning compositions and shampoos, preferably being 0.1 to 3% and more preferably 0.1 or 0.3 to 0.7% or 1%. The long chain saturated primary alcohol and/or "derivatives" thereof will normally total 0.5 to 10%, preferably 0.5 to 5 or 6%, more preferably 1 to 5%. The content of aqueous medium (which may include various adjuvants) will normally be in the range of 75 to 99%, with the water content of such a shampoo being 60 to 90%, preferably 63 to 85%, and more preferably 63 to 80%. However, the water and aqueous medium contents may be varied, depending on the proportions of adjuvants desirably present in the composition. Normally the ratio of contents of long chain saturated primary alcohol and/or "derivatives" to conditioning agent(s) will be in the range of 0.2 to 5, preferably in the range of 0.3 to 3, with ratios of 0.5 to 2 and about 1 being more and most preferred, respectively.

In various shampoo compositions within the invention the proportions of components may be varied within the ranges given, as will be indicated by the following ranges of proportions of the components of some different types of preferred compositions.

For a shampoo comprising lipophile sulfates, quaternary ammonium salt, aminosilicone and long chain saturated primary alcohol, in water, there will usually be present 5 to 18% of fatty alcohol sulfate, preferably as its ammonium salt, 0 or 1 to 10% of fatty alcohol ether sulfate, preferably as its sodium salt (and the range of ratios can be 1:10 to 10:1), 0.2 to 2% of quaternary ammonium salt, 0.5 to 10% of the aminosilicone, 0.5 to 5 or 6% of the long chain saturated primary alcohol and/or its "derivatives", 65 to 85% of water and any balance of shampoo adjuvant(s) Preferred ranges are 10 to 15% or 20%, 0 or 1 to 5%, 0.1 to 0.7%, 0.8 to 4%, 1 to 5.0% and 63 to 80%, respectively. Such compositions may also comprise 0.2 to 2% of hydroxyethyl cellulose (or other suitable thickener), 2 to 5% of lauric monoethanolamide or cocodiethanolamide, 0 or 0.5 to 2% of microcrystalline wax and 0 or 0.5 to 1% of petrolatum.

For another such composition the first six of the ranges will be the same as immediately previously mentioned but there will also be present 0.3 to 2% of polyethylene and 0.3 to 2% of mineral oil, preferably 0.5 to 1.5% and 0.5 to 2%, respectively. The hydroxyethyl cellulose and lauric monoethanolamide components are in the same proportions as given for the previous formulas but 0.1 to 2%, preferably 0.1 to 1% of paraffin wax and 0.1 to 2%, preferably 0.1 to 0.5% of isoparaffin are also present.

In an additional embodiment of the invention, wherein the shampoo includes polyethylene as the basic hair conditioning agent, together with quaternary ammonium halide, and with a high molecular weight lipid solubilizing agent, such as mineral oil, to solubilize the polyethylene, the proportions of components are like those previous given for the anionic detergents, the cationic conditioner, the long chain saturated primary alcohol and/or "derivatives" thereof, the water and any adjuvants present. However, in such composition the aminosilicone can be omitted and the proportion of alkoxylate detergent may be increased to 15% wile proportions of polyethylene and mineral oil will normally be 0.3 to 2% for each, and preferably will be in the ranges of 0.5 to 1.5 and 0.5 to 2%, respectively. Other components which are also desirably present include 0.2 to 2% of hydroxyethyl cellulose, 2 to 5% of lauric monoethanolamide, 0.1 to 1% of paraffin wax and 0.1 to 0.5% of isoparaffin.

In a further shampoo of the invention the proportions of the anionic detergents, cationic surfactant, aminosilicone, long chain saturated primary alcohol and or "derivatives", other adjuvants and water are the same as in the first of these types of formulas given except for the fact that the long chain saturated primary alcohol present (which may include a derivative thereof) preferably comprises 0.5 or 1 to 2 or 3% of a chain length averaging about 30 carbon atoms and to 2 or 3% of a chain length averaging about 40 carbon atoms. In a modification of that formula there is also present 0.5 to 2% of a polyethoxylated long chain saturated primary alcohol (a "derivative") wherein the alcohol is of an average of about 40 carbon atoms and is ethoxylated with 10 to 20 moles, e.g., 13 moles, of ethylene oxide per mole. Both such formulas, which include no gum or gum-like material (hydroxyethyl cellulose) may be supplemented with 2 to 5% of lauric monoethanolamide, 0.5 to 2% of $C_{18-36}$ acid triglyceride and 0.1 to 0.5% of citrate, preferably sodium citrate. A further modification of the immediately preceding formula includes the presences, as hair conditioning agents, of 0.1 to 1% of paraffin wax and 0.5 to 1.5% of normally solid polyethylene of a molecular weight in the range of 1,000 to 4,000, with 0.5 to 2% of mineral oil of a molecular weight in the range of 300 to 800, present as a solvent medium for the polyethylene.

Other preferred formula types comprise the same proportions of anionic detergents, cationic surfactant, aminosilicone, long chain saturated primary alcohol, water and shampoo adjuvant(s), as in the immediately preceding formula, but also include as a supplementing conditioning agent, 0.25 to 5% of $C_{18-36}$ (mixed) acid triglyceride. Such composition may also include 2 to 5% of lauric monoethanolamide, 0.2 to 2% of hydroxyethyl cellulose, 0.5 to 2% of microcrystalline wax and 0.5 to 1% of petrolatum. Instead of the microcrystalline wax and petrolatum there may be substituted 0.5 to 1.5% of the previously described polyethylene and 0.5 to 2% of the described mineral oil.

For gels, pastes, thicker cremes and cake materials within the invention the required, optional and adjuvant components will normally be in the same ranges of proportions as in the aqueous compositions, with the proportion of water often being decreased, sometimes to as low as 30 or 40%. Also, the water may be replaced, up to 50% thereof in some instances, but usually to no more than 20%, by another solvent, e.g., ethanol or isopropanol.

Although the fiber conditioning and hair conditioning compositions of this invention may be in the various physical forms mentioned, preferably they are in liquid form (of lotion appearance) and the most preferred embodiment of the invention is a liquid hair conditioning shampoo. Such compositions should be stable chemically and physically to be acceptable in the marketplace. They should not deteriorate to an unacceptable extent on storage, and should not have components settle out or phases separating during storage. The presence of the mentioned long chain primary alcohols (of the Unilin or Unithox type[s]) stabilizes the invented compositions, in addition to giving them an attractive pearlescent appearance and improving fiber conditioning. Also, such shampoos are of desirable viscosities, so as to be pourable, and yet will not be so thin that they run uncontrollably. The desired viscosity range is 1,000 to 15,000 centipoises at room temperature (25° C.), preferably 3,000 to 6,000 centipoises. The invented shampoos are non-settling and non-separating, and do not chemically deteriorate on storage, as has been established by accelerated aging tests at elevated temperatures. The shampoo viscosity may change slightly on storage but such a change does not significantly affect the shampoo's properties. Also, the desired use viscosity can be obtained by manufacturing a shampoo at a certain viscosity which allows for any expected viscosity change before use.

The improved hair conditioning obtained by use of the invented compositions, compared to controls, from which the mentioned conditioning agents have been omitted is very noticeable to even the casual user of the invented shampoo or other conditioning composition, and is measurable in standard tests that are used to evaluate conditioning and its components, including ease of wet combing, ease of dry combing, manageability, static charge retention and flyaway. The casual shampooer will note that the hair is easier to comb after shampooing, in both wet and dry states, compared to control hair washed with a shampoo that is not under the invention (with conditioning components or some of them missing from it). Scientific tests also prove that the force needed to move a comb through a standard hair tress after treatment (shampooing) of the hair with an invented shampoo, and rinsing, is measurably less than that when such a control is employed in the same manner. Such results are confirmed by panel tests, in which several experienced evaluators, using both the experimental and control products in blind tests, evaluate them for such combing ease, manageability and static characteristics and effects.

Uses of the invented compositions, including the shampoos, are not required to be different from normal uses of hair conditioning shampoos and other fiber conditioning compositions. Conditioning compositions maybe applied at room temperature or at somewhat elevated temperatures in normal quantities and may be left on the hair for different lengths of time, depending on the extent of conditioning desired. Usually the conditioning agent and the hair will be at a temperature in the range of 15° to 50° C., preferably 20° to 40° C., and the conditioning composition will be in contact with the hair for from 30 seconds to ten minutes, preferably one to five minutes. The amount of composition applied will normally be in the range of 0.1 to 25 grams, often being 0.2 to 10 g. or 0.5 to 2 or 5 g., on the basis of the non-aqueous and non-solvent components of the composition. On the basis of the shampoo which may be employed such application rates may be in the range of 0.5 to 50 grams, often 2 to 15 or 20 grams and frequently five or ten grams per use. The applied conditioning composition may be brushed and/or combed through the hair and may be subsequently washed out, may be allowed to remain on the hair or may be partially removed, as by towelling. When the shampoo is employed to wash and condition the hair it will be rinsed off with water after remaining on the hair as an aqueous foam for a sufficient length of time, usually 1 to 5 minutes, so as satisfactorily to condition the hair, and may then be wet combed, dried, as by blow drying, and dry combed or brushed to the desired style.

To manufacture the present compositions, including shampoos, no complex procedures have to be followed, but to obtain best stability and pearlescence, and greatest conditioning activity, after storage of the invented compositions, it will be desirable to form a dispersion of the water soluble lipophile sulfate and/or sulfonate detergent(s) and adjuvants in water at an elevated temperature, such as 70° to 95° C., dissolve and/or disperse cationic conditioning agent, such as quaternary ammonium salt, with any lipophilic materials, such as hydrocarbons, including polyethylene, mineral oil, microcrystalline wax, petrolatum, paraffin and isoparaffin, long chain alcohol, triglyceride and stearyl stearate as a melt or liquid mix at elevated temperature, and admix the two mixes at such elevated temperature, after which the heated aminosilicone may be admixed with the resulting mix (it may sometimes also be included with the lipophiles), with the various mixings taking place with the portions to be mixed at approximately the same temperatures. It is sometimes desirable for the aminosilicone to be mixed in after the main pre-mixing to promote better stability of the product. When adjuvants are present those which are water soluble and/or dispersible may be mixed in with the aqueous phase materials and those which are not water soluble or dispersible in the aqueous medium may be blended in with the lipophilic materials, such as the hydrocarbons, or in some instances may be added to the mixture of the hydrophilic and lipophilic materials either before or after cooling to :room temperature. Normally perfume will be added to the other mixed components after cooling to room temperature and the aminosilicone will be added at elevated temperature and before such cooling. The perfume is added to the cooled composition to avoid losses thereof due to volatilizations of components and to prevent any degradation due to heating it. When the procedure described is not followed, as when the various components of the compositions are blended indiscriminately, unstable products may result, which can separate or settle out on storage, and such unstable compositions tend to have poorer conditioning properties than the stable conditioning compositions and shampoos that are made according to the invented procedure.

The following examples illustrate but do not limit the invention. Unless otherwise indicated all parts are by weight and all temperatures are in degrees Centigrade in the examples, other parts of the specification, and in the claims.

EXAMPLE 1

| Component | % (by weight) | | |
|---|---|---|---|
| | 1A | 1B | 1C |
| Ammonium lauryl sulfate | 12.50 | 12.50 | 12.50 |
| Sodium lauryl ether sulfate (2 EtO per mole) | 2.50 | 2.50 | 2.50 |
| Distearyl dimethyl ammonium chloride | 0.50 | 0.50 | 0.50 |
| Aminosilicone A (Dow-Corning) | 2.50 | — | 1.50 |
| Long chain alcohol (Unilin TM 425, Petrolite Corp.) | 2.50 | 2.50 | 2.50 |
| Polyethylene (M.W. = 2,000, Allied Corp.) | — | 0.75 | 0.75 |
| Microcrystalline Wax (M.P. = 82° C.) | 1.00 | — | — |
| Paraffin wax (M.P. = 53° C., Boler Petroleum Corp.) | — | 0.35 | 0.35 |
| Isoparaffins (Isopar TM M, Exxon Corp.) | — | 0.25 | 0.25 |
| Petrolatum, white (Alba Protopet TM) | 0.75 | — | — |
| Mineral oil (Britol TM 50, Boler Petroleum Corp.) | — | 1.00 | 1.00 |
| Hydroxyethyl cellulose 250 HHR (Aqualon Corp.) | 0.57 | 0.67 | 0.67 |
| Hydroxyethyl cellulose 330 CS (Aqualon Corp.) | 0.18 | 0.23 | 0.23 |
| Lauric monoethanolamide | 3.50 | 3.50 | 3.50 |
| Sodium chloride | 0.20 | 0.20 | 0.20 |
| Preservative (Germaben TM II) | 0.50 | 0.50 | 0.50 |
| Perfume | 0.80 | 0.80 | 0.80 |
| Colorant | 0.10 | 0.10 | 0.10 |
| Deionized water | 71.90 | 73.65 | 72.15 |
| | 100.00 | 100.00 | 100.00 |

Compositions of Formulas 1A, 1B and 1C are made by the method described in the specification, with mixings of the hydrophilic components, separate mixings of the lipophilic components and admixings thereof, all conducted at elevated temperature, e.g., 80° C., followed by admixings of the aminosilicone components, when present, and sodium chloride, to adjust the viscosity, and final addition of perfume after cooling of the unperfumed shampoo to about room temperature (25° C.), which is when pearlescence occurs.

The products made are all attractively pearlescent liquid shampoos of viscosities in the range of 3,000 to 6,000 centipoises at 25° C. and of pH's in the range of 6 to 7, and are all found to be stable by elevated temperature storage tests, with no appreciable separation or settling out of components. When tested for hair conditioning capabilities, according to the tests described in the specification, they are found to be good conditioning shampoos, all being better than controls that do not contain the water insoluble conditioning agents present in the given formulas. The conditioning obtained from each of the described formulas is at least equivalent to the best of all the commercial conditioning shampoos presently on the market and the shampoo of Formula 1C is even measurably and significantly better in conditioning action than such commercial product.

When the anionic detergent component is removed from the 1C formula the hair conditioning (and fiber conditioning) composition resulting is useful for the treatment of fibrous materials and may be employed as a rinse for human hair. In both such applications, even after rinsing off the product with water the fibrous material treated will be of lower static charge, will be soft and pliant to the touch, and will be glossy and attractive in appearance. Also, when human hair is so treated it will be less subject to objectionable "flayaway" and will be more readily combable and manageable.

In other modifications of Formulas 1A, 1B and 1C, which are also outside this invention, like the modification of Formula 1C mentioned above, when the long chain alcohol is omitted from the formulas and is replaced by deionized water the shampoo tends to become unstable and to separate into different phases and/or have components thereof settle out on elevated temperature storage. Also, hair conditioning is not as good and pearlescence is either non-occurring or is diminished and less attractive.

When Aminosilicone A is replaced by conventional nonvolatile silicones or other aminosilicones in Formulas 1A and 1C conditioning activity is noticeably diminished (but is still present). Such activity for Formula 1C may be increased further by adding 1% of Aminosilicone A to the formula in replacement of 1% of the deionized water, so as to increase the percentage of Aminosilicone A to 2.50%, equal to that of Formula 1A. Similarly, when 2.50% of Aminosilicone A is added to the formula of Example 1B in place of a like percentage of water, conditioning is also substantially improved.

EXAMPLE 2

| Component | % (by weight) | | |
|---|---|---|---|
| | 2A | 2B | 2C |
| Ammonium lauryl sulfate | 12.50 | 12.50 | 12.50 |
| Sodium lauryl diethoxy sulfate | 2.50 | 2.50 | 2.50 |
| Distearyl dimethyl ammonium chloride | 0.50 | 0.50 | 0.50 |
| Aminosilicone A (Dow-Corning) | 1.50 | — | 1.50 |
| Long chain linear alcohol (Unilin 425, Petrolite Corp.) | 1.50 | 1.50 | 1.50 |
| Long chain linear alcohol (Unilin 550, Petrolite-Corp.) | 1.00 | 1.00 | 1.00 |
| Long chain linear alcohol ethoxylate (Unithox TM 550, Petrolite Corp.) | 1.00 | 1.00 | 1.00 |
| $C_{18-35}$ triglyceride (Syncrowax HGL-C, Croda Corp.) | 1.00 | 1.00 | 1.00 |
| Paraffin wax (M.P. = 53° C., Boler Petroleum Corp.) | — | 0.35 | 0.35 |
| Polyethylene 617-A (Allied Corp.) | — | 0.75 | 0.75 |
| Mineral oil (Britol 50, Boler Petroleum Corp.) | — | 1.00 | 1.00 |
| Isoparaffin (Isopar M, Exxon Corp.) | — | 0.25 | 0.25 |
| Lauric monoethanolamide | 3.50 | 3.50 | 3.50 |
| Preservative (Germaben II) | 0.50 | 0.50 | 0.50 |
| Sodium citrate | 0.25 | 0.25 | 0.25 |
| Perfume | 0.80 | 0.80 | 0.80 |
| Colorant | 0.10 | 0.10 | 0.10 |
| Deionized water | 73.35 | 72.50 | 71.00 |
| | 100.00 | 100.00 | 100.00 |

The shampoo compositions of this example are made by the method described in Example 1 and elsewhere in the specification, and it is found that all the shampoos made are attractively pearlescent and are stable under elevated temperature storage conditions. Additionally, they are excellent hair conditioning shampoos, equalling or exceeding shampooing and hair conditioning properties of the best commercial hair conditioning shampoo on the market, with Formulas 2A and 2B equalling such conditioning power and Formula 2C surpassing it. The three shampoos made are of desired viscosity and pH, like those of the compositions of Example 1.

EXAMPLE 3

| Component | % (by weight) | |
|---|---|---|
| | 3A | 3B |
| Ammonium lauryl sulfate | 12.50 | 12.50 |
| Sodium lauryl ethoxylate sulfate (2 EtO) | 2.50 | 2.50 |
| Distearyl dimethyl ammonium chloride | 0.50 | 0.50 |
| Aminosilicone A (Dow-Corning) | 1.50 | 1.50 |
| Long chain alcohol (Unilin 425) | 1.00 | 1.00 |
| Microcrystalline wax | 1.00 | — |
| Petrolatum, white | 0.75 | — |
| Syncrowax HGL-C (Croda Corp.) | 0.75 | 0.75 |
| Polyethylene 617-A (Allied Corporation) | — | 0.75 |
| Mineral oil (Britol-50) | — | 1.00 |
| Lauric monoethanolamide | 3.50 | 3.50 |
| Hydroxyethyl cellulose | 0.75 | 0.75 |
| Preservative (Germaben II) | 0.50 | 0.50 |
| Colorant | 0.10 | 0.10 |
| Perfume | 0.80 | 0.80 |
| Deionized water | 73.85 | 73.85 |
| | 100.00 | 100.00 |

Shampoo compositions of this example are made in the same manner as described in Examples 1 and 2, and in the preceding specification (and also in U.S. patent application Ser. No. 07/432,952). The two shampoos made both utilize long chain saturated primary alcohol of the Unilin 425 type in conjunction with $C_{18-36}$ (mixed) triglyceride, aminosilicone and polyethylene or with aminosilicone, microcrystalline wax and petrolatum, as water insoluble conditioning agents. The shampoos made are attractively pearlescent and are stable on elevated temperature storage. Additionally, they are of improved hair conditioning properties, with the 3B formula being even better in hair conditioning than the 3A formula. When the amounts of the Aminosilicone A and Unilin 425 are increased, to 2.50% and 2.00%, at the expense of the deionized water, conditionings are improved even further, and stabilities and pearlescences are still excellent.

EXAMPLE 4

| Component | % (by weight) | | | |
|---|---|---|---|---|
| | 4A | 4B | 4C | 4D |
| Ammonium lauryl sulfate | 12.50 | 12.50 | 12.50 | 12.50 |
| Sodium lauryl diethoxy sulfate | 2.50 | 2.50 | 2.50 | 2.50 |
| Distearyl dimethyl ammonium chloride | 0.50 | 0.50 | 0.50 | 0.50 |
| Aminosilicone A (Dow-Corning) | 1.50 | 1.50 | 1.50 | — |
| Long chain ($C_{30\ average}$) alcohol | 2.50 | 2.50 | 1.50 | 2.50 |
| Long chain ($C_{40\ average}$) alcohol | — | — | 1.00 | — |
| Unithox 550 long-chain ($C_{40\ average}$) alcohol ethoxylate (13 EtO) | — | — | 1.00 | — |
| Microcrystalline wax | 1.00 | — | — | — |
| Petrolatum, white | 0.75 | — | — | — |
| Syncrowax HGL-C | — | — | 1.00 | — |
| Polyethylene 617-A (Allied Corp.) | — | 0.75 | — | 0.75 |
| Paraffin wax (M.P. = 53° C.) | — | 0.35 | — | 0.35 |
| Mineral oil (Britol 50) | — | 1.00 | — | 1.00 |
| Isopar M | — | 0.25 | — | 0.25 |
| Lauric monoethanolamide | 3.50 | 3.50 | 3.50 | 3.50 |
| Hydroxyethyl cellulose 250 HHR | 0.57 | 0.67 | — | 0.67 |
| Hydroxyethyl cellulose 330 CS | 0.18 | 0.23 | — | 0.23 |
| Preservative | 0.50 | 0.50 | 0.50 | 0.50 |
| NaCl | 0.20 | 0.20 | 0.20 | 0.20 |
| Sodium citrate | — | — | 0.25 | — |
| Colorant | 0.10 | 0.10 | 0.10 | 0.10 |
| Perfume | 0.80 | 0.80 | 0.80 | 0.80 |
| Deionized Water | 72.90 | 72.15 | 73.15 | 73.65 |
| | 100.00 | 100.00 | 100.00 | 100.00 |

The compositions of this example are made in the same manner as described in Examples 1–3 and in U.S. patent application Ser. No. 07/432,952. The products resulting, all of which contain a long chain alcohol or derivative of type(s) described herein which improve(s) conditioning and stability and make(s) the shampoo pearlescent, are all attractive pearlescent liquids of the range of 6 to 7 and viscosities in the rage of 3,000 to 6,000 centipoises at 25° C. All are of improved stability, compared to compositions which do not contain the long chain alcohol or derivative thereof, and all are excellent cleaning agents and conditioners for hair. It will be noted that all the compositions contain the preferred long chain $C_{30\ average}$ alcohol, with Formula 4C also including the corresponding $C_{40\ average}$ alcohol and an ethoxylated such alcohol.

Formula 4C also contains no gums and relies for conditioning primarily on Aminosilicone A, the long chain alcohols, the "derivative" thereof, and long chain fatty acid triglyceride (Syncrowax). Best conditioning and stabilizing effects are obtained with Formula 4C but all of the four compositions are excellent conditioning shampoos, competitive in desirable conditioning properties, stability and appearance with the best commercial conditioning shampoos that are on the market.

EXAMPLE 5

In preceding Examples 1–4 the preferred ammonium lauryl sulfate and sodium lauryl ethoxy sulfate mixtures were employed but similar results are obtainable when other higher alkyl sulfates, such as the sodium and triethanolamine salts of $C_{14-18}$ alkyl sulfuric acids, are employed. Similarly, the sodium lauryl ethoxy sulfate can be replaced by sodium $C_{14-18}$ ethoxy sulfates wherein the ethoxy group is of 1 or 2 to 5 or 6 carbon atoms, preferably 3, and the sodium is replaced by ammonium or triethanolamine. In like manner the distearyl dimethyl ammonium chloride may be replaced by other quaternary ammonium salts, such as tricetyl methyl ammonium bromide or chloride, dilauryl diethyl ammonium chloride and sometimes even by trimethyl stearyl ammonium chloride or the corresponding tallowyl compound (in which the alkyl is that obtained from beef tallow). Variations in the other water insoluble hair conditioning agents may be made, utilizing other embodiments of such materials within the description given in the specification, including other ethoxylated long chain primary alcohols of an average of 24 to 40 carbon atoms in the alcohol chain, and corresponding esters and acids. Various adjuvants may be substituted for those in the given formulas. For example, the monoethanolamide may be replaced by lauric myristic mono- or diethanolamide or the corresponding coco alkanolamide, or by corresponding isopropanolamides, EDTA may be included, and the hydroxylated ethyl celluloses may be replaced by hydroxylated propylmethyl celluloses, methyl cellulose or other suitable gums or thickeners. In such cases the compositions made will be of high quality and will be satisfactorily conditioning, stable and attractively pearlescent shampoos of desired pH and viscosity. Similarly, when the anionic detergent(s) is/are omitted from the formula conditioning rinses and fiber conditioners are obtainable which will be of similar properties and which satisfactorily condition fibrous materials, such as hair, in the manner described. Such compositions may be in liquid, gel, paste or creme form.

EXAMPLE 6

| Component | % (by weight) A | B |
|---|---|---|
| Part I | | |
| Irradiated deionized water | 72.19 | 71.89 |
| Hydroxyethyl cellulose (Natrosol 250 HHR) | 0.20 | — |
| Ammonium lauryl sulfate | 15.00 | 15.00 |
| Monobasic ammonium phosphate (buffer) | 0.10 | 0.10 |
| Part II | | |
| Unilin 425 | 3.00 | 3.00 |
| Cocodiethanolamide | 4.00 | 5.00 |
| Part III | | |
| Aminosilicone A | 3.00 | 3.00 |
| Part IV | | |
| Perfume (CP Paris K3-157 new revised 3) | 0.80 | 0.80 |
| Sodium chloride | 0.50 | — |
| | 100.00 | 100.00 |

In essentially the same manner previously described, the components of each of Parts I and II were separately mixed and were then admixed at 90° C., followed by sequential additions thereto of Parts III and IV, with the addition of Part IV being at room temperature. The shampoos made are both pearlescent and attractive in appearance, and are of desired viscosity and pH. Both condition hair washed with them as well as or better than the most effective of the leading hair conditioning shampoos on the U.S. market at present.

In the formula given the quantity of Aminosilicone A is on the basis of pure aminosilicone, although it was employed together with one part of a solvent for the silicone per three parts of silicone, so as to reduce its viscosity (and such was also employed in the other Examples, in which the quantities are also on the basis of the pure aminosilicone. Also, the ammonium phosphate buffer may be employed in a proportion up to 0.20% in these formulas.

In a variation of the formula, instead of employing Unilin 425, Unilin 550 or pure long chain linear saturated alcohols of 30 or 36 carbon atoms to the molecule (or a mixture thereof) may be substituted and the results are equivalent. However, further improvements in conditionings may be obtained by incorporation in the formulas of quaternary ammonium salt, e.g., distearyl dimethyl ammonium chloride, and other conditioning agents, e.g., microcrystalline wax, petrolatum, polyethylene and beeswax. Also, the aminosilicone may be replaced by non-aminosilicones and dimethicones, such as the silicones of U.S. Pat. No. 4,704,272, and other non-volatile (preferred) water insoluble silicones.

EXAMPLE 7

The compositions of the preceding examples may be further modified, by changing the proportions of the various components thereof ±10%, ±20% and ±30%, while maintaining them within the ranges recited elsewhere in the specification, and the modified compositions resulting will be stable, pearlescent shampoos and fiber conditioning products of improved hair conditioning and fiber conditioning properties. When such are employed to shampoo the hair or are used as conditioning hair rinses, according to the processes described in this specification, which include application to the fibrous material or hair, often in the presence of additional water, followed by rinsing, the hair is satisfactorily cleaned and conditioned. It may be combed more readily when wet or dry, will not accumulate objectionable static charges and will be manageable and softer to the touch.

The compositions of this invention, as represented by the formulas and descriptions given in the preceding examples, are significant advances in the fiber conditioning and hair conditioning arts. By utilizing the described long chain primary alcohol, which is preferably completely saturated, or its "derivative(s)", in conjunction with the described water insoluble conditioning agent(s)(and cationic surfactant), it has been possible to make greatly improved hair conditioning compositions, such as shampoos, which are as good as or better in conditioning properties than any such compositions previously marketed. Such has been accomplished by utilizing the mentioned long chain alcohols or their derivatives, such as the Unilins and Unithoxes, which are available materials but which were heretofore not known as components of hair conditioning compositions or shampoos.

The various patents, patent applications and publications previously referred to in this specification are hereby incorporated herein by reference.

This application is a continuation-in-part of U.S. patent applications Ser. Nos. 07/432,644 and 07/432,952, which are both continuations-in-part of Ser. No. 07/369,361.

The invention has been described with reference to illustrations and examples thereof but is not intended to be limited to these because it is evident that one of skill in the art, with the present specification before him or her, will be able to utilize substitutes and equivalents without departing from the invention.

What is claimed is:

1. A stable hair conditioning shampoo in emulsion or suspension form which comprises 1 to 35% of a synthetic organic detergent, 0.3 to 10% of a water insoluble hair conditioning agent, and a stabilizer comprising a long chain primary alcohol having an average of from about 30 to 45 carbon atoms in the chain or alkoxylated derivatives thereof, said alcohol or derivative thereof being present in sufficient proportion to stabilize the emulsion or suspension, and 60 to 90% of an aqueous medium, with the ratio of content of the long chain alcohol or derivative thereof to the conditioning agent being in the range of from about 0.2 to 5:1.

2. The shampoos of claim 1 wherein said detergent is anionic.

3. The shampoo of claim 2 wherein said anionic detergent is selected from the group consisting of ammonium fatty alcohol sulfates, ammonium fatty alcohol alkoxy sulfates and mixtures thereof.

4. The shampoo of claim 2 wherein said conditioning agent is a silicone.

5. The shampoo of claim 4 wherein said silicone is a polysiloxane.

6. The shampoo of claim 4 wherein said silicone is an aminopolysiloxane.

7. The shampoo of claim 2 wherein said stabilizer is present in said shampoo at a level of 0.5 to 10% by weight.

8. The shampoo of claim 2 wherein said stabilizer is primary alcohol having an average of from about 30 to about 40 carbon atoms in the chain.

9. The shampoo of claim 2 wherein said stabilizer is the alkoxylated derivative containing up to about 20 alkoxy groups per mole.

10. The shampoo of claim 2 wherein said stabilizer comprises a mixture of a primary alcohol having an average of about 30 carbon atoms in the chain and a primary alcohol having an average of about 40 carbon atoms in the chain.

11. The shampoo of claim 2 further containing from about 0.2 to about 2% by weight of hydroxyethyl cellulose.

12. The shampoo of claim 11 which further contains from about 2 to about 5% by weight of a foam modifier selected from the group consisting of lauric monoethanolamide and cocodiethanolamide.

13. The shampoo of claim 2 further containing from about 0.2 to about 2% by weight of a quaternary ammonium salt.

14. The shampoo of claim 8 wherein at least 80% by weight of the chains in said alcohol range from about 20 to about 44 carbon atoms.

15. The shampoo of claim 8 wherein at least 80% by weight of the chains in said alcohol range from about 28 to about 54 carbon atoms.

16. A stable, hair conditioning shampoo in emulsion or suspension form which comprises a mixture of 2 to 35% by weight of ammonium lauryl sulfate, 0.5 to 10% by weight of a primary alcohol having an average chain length of about 30 carbon atoms wherein at least 80% by weight of said alcohol chains range from 20 to 44 carbon atoms, 0.3 to 10% of a dimethicone conditioning agent, up to 2% by weight of hydroxyethylcellulose, up to 5% by weight of cocodiethanolamide and from about 60 to 90% by weight water, wherein the weight ratio of the content of said alcohol to said conditioning agent lies in the range of from about 0.5 to 2:1.

17. A process for shampooing and conditioning hair which comprises applying to human hair, on the head, a shampooing and conditioning proportion of a shampoo according to claim 22, and rinsing the shampoo from the hair, thereby leaving on the hair a conditioning amount of conditioning agent.

* * * * *